(12) United States Patent
Foster et al.

(10) Patent No.: US 7,045,624 B2
(45) Date of Patent: May 16, 2006

(54) COMPOUNDS AND THEIR USES

(75) Inventors: Alison Jane Foster, Bebington (GB); Cornelius Paul Erik Van Der Logt, Vlaardingen (NL); Erwin Werner Tareilus, Vlaardingen (NL)

(73) Assignee: Conopco, Inc., Edgewater, NJ (US)

( * ) Notice: Subject to any disclaimer, the term of this patent is extended or adjusted under 35 U.S.C. 154(b) by 0 days.

(21) Appl. No.: 10/664,367

(22) Filed: Sep. 17, 2003

(65) Prior Publication Data

US 2004/0067970 A1 Apr. 8, 2004

(30) Foreign Application Priority Data

Sep. 18, 2002 (GB) ................................. 0221697.6

(51) Int. Cl.
*C07D 237/02* (2006.01)
*C07D 239/02* (2006.01)

(52) U.S. Cl. ...................... 544/224; 544/242; 544/245

(58) Field of Classification Search ................ 544/224, 544/242, 245
See application file for complete search history.

(56) References Cited

U.S. PATENT DOCUMENTS 3,821,221 A * 6/1974 Podesva ...................... 544/316

FOREIGN PATENT DOCUMENTS

JP 08087120 * 1/1996

OTHER PUBLICATIONS

Wei et al, "AG-3-5: A chemical producing sensations of cold", Journal of Pharmacy and Pharmacology (1983), 35(2), 110-112.*

Briffa, K. et al., *Blowing Hot and Cold*, Science, vol. 295; pp. 2227-2228, (2002).

Kim, C-H et al., *Synthesis of Pyrimidin-2-one Nucleosides as Acid-Stable Inhibitors of Cytidine Deaminase*, J. Med. Chem., 29:1364-1380, (1986).

McKerny, D. et al., *Identification of a cold receptor reveals a general role for TRP channels in thermosensation*, Nature, vol. 416; pp. 52-58, (2002).

Wei, E.T., et al.; *AG-3-5: a chemical producing sensations of cold*; J. Pharm. Pharmacol.; 35:110-112 (1983).

www.tocris.com/1531.htm printout—*An Activator of the Novel Cold Receptor, CMR1*.

* cited by examiner

*Primary Examiner*—James O. Wilson
*Assistant Examiner*—Paul V. Ward
(74) *Attorney, Agent, or Firm*—Michael P. Aronson

(57) ABSTRACT

Use of a compound according to Formula [I]:

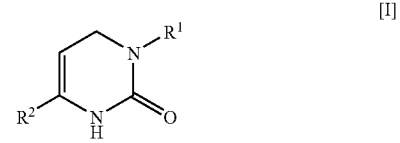

or a salt thereof to produce a cooling sensation, wherein $R^1$ and $R^2$ are independently selected from hydrogen or halogen atoms; hydroxy, cyano, nitro, mercapto, carbonyl, sulfone and carboxy groups; or optionally substituted alkyl, alkenyl, alkoxy, alkylthio, aryl, aryloxy, arylthio, amino, siloxy, ester and heterocyclic groups, with the proviso that when $R^1$ is 2-hydroxyphenyl, $R^2$ is other than 3-nitrophenyl.

9 Claims, No Drawings

COMPOUNDS AND THEIR USES

FIELD OF THE INVENTION

The invention relates to compounds which are capable of producing a cooling sensation when they are brought into contact with the human body. Such compounds have applications in many fields, particularly in oral and personal hygiene products and foodstuffs.

BACKGROUND OF THE INVENTION

Tetrahydropyrimidine-2-one compounds are known to be useful in pharmaceutical preparations. For example, U.S. Pat. No. 3,821,221 discloses a number of such compounds, and their effect as central nervous system stimulants or depressants. The compounds are said to be of value for therapeutic applications as potential psychotropic drugs.

As a result of pharmacological research into these tetrahydropyrimidine-2-one derivatives, it was discovered that icilin (also known as AG-3-5, chemical name 1-[2-hydroxyphenyl]-4-[2-nitrophenyl]-1,2,3,6-tetrahydropyrimidine-2-one) produced sensations of coldness when in contact with mucous membranes (nostrils, lips and eyelids) of the researchers, and also when ingested (see Wei et al, *J. Pharm. Pharmacol.* 1983, 35:110–112).

A known compound for producing a sensation of cold is menthol (2-isopropyl-5-methyl-cyclohexanol), which has been extensively applied as an additive in, for example, foodstuffs and oral hygiene products. It is used primarily because it elicits a sensation of coolness in the mouth, and because it has a pleasing mint flavour and odour. The cooling effect of menthol is due to the action of menthol on the nerve endings of the human body which detect hot and cold stimuli. In particular, menthol is believed to activate cold receptors on nerve endings. However, the use of menthol is limited by its strong minty smell and relative volatility.

It was found that icilin was capable of producing the same cooling effect as menthol. Icilin has a number of advantages over menthol, for example it is more potent, and has a lower acute toxicity, due to its lack of anaesthetic properties. Icilin was considered to be a particularly useful compound for pharmacological applications because it lacks the flavour and odour of menthol and is not readily absorbed through the skin. However, icilin has not been disclosed as a replacement for menthol for non-pharmaceutical applications.

DEFINITION OF THE INVENTION

According to a first embodiment of the invention, there is provided the use of a compound according to Formula [I]:

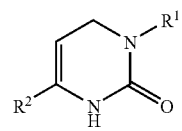

[I]

or a salt thereof to produce a cooling sensation, wherein $R^1$ and $R^2$ are independently selected from hydrogen or halogen atoms; hydroxy, cyano, nitro, mercapto, carbonyl, sulfone and carboxy groups; or optionally substituted alkyl, alkenyl, alkoxy, alkylthio, aryl, aryloxy, arylthio, amino, siloxy, ester and heterocyclic groups, with the proviso that when $R^1$ is 2-hydroxyphenyl, $R^2$ is other than 3-nitrophenyl.

According to a second embodiment of the invention, there is provided a compound of formula [IV]:

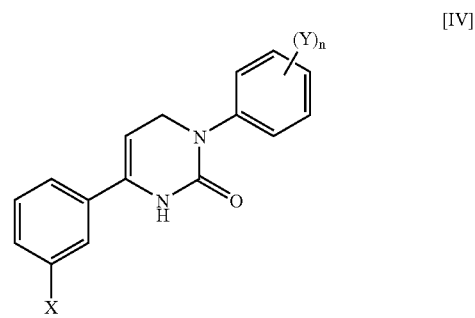

[IV]

or a salt thereof, wherein X is a hydrogen or halogen atom, or an alkyl or alkoxy group; Y is hydroxy or alkoxy; and n is 0, 1, 2 or 3, with the proviso that when n is 1 and Y is hydroxy, X is alkyl or hydroxy.

A third embodiment of the invention provides a composition comprising a compound of formula [I]:

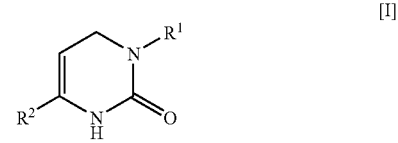

[I]

or a salt thereof to produce a cooling sensation, wherein $R^1$ and $R^2$ ar independently selected from hydrogen or halogen atoms; hydroxy, cyano, nitro, mercapto, carbonyl, sulfone and carboxy groups; or optionally substituted alkyl, alkenyl, alkoxy, alkylthio, aryl, aryloxy, arylthio, amino, siloxy, ester and heterocyclic groups.

A fourth embodiment of the present invention provides a method of imparting a cooling sensation to a human comprising administering, preferably orally, to said human, a compound according to Formula [I]:

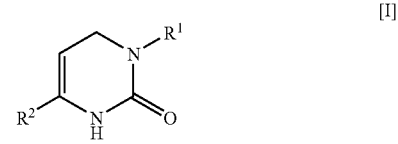

[I]

wherein $R^1$ and $R^2$ are independently selected from hydrogen or halogen atoms; hydroxy, cyano, nitro, mercapto, carbonyl, sulfone and carboxy groups; or optionally substituted alkyl, alkenyl, alkoxy, alkylthio, aryl, aryloxy, arylthio, amino, siloxy, ester and heterocyclic groups, with the proviso that when $R^1$ is 2-hydroxyphenyl, $R^2$ is other than 3-nitrophenyl.

DETAILED DESCRIPTION OF THE INVENTION

Unless otherwise specified in the following description, alkyl represents a linear or cyclic saturated hydrocarbon which may be straight-chain or branched, and preferably contains up to 20 carbon atoms. Similarly, alkenyl represents a linear or cyclic, straight-chain or branched unsaturated hydrocarbon which preferably contains up to 20 carbon atoms. When an alkyl group is linear, it preferably contains from 1 to 10, more preferably from 1 to 6 carbon atoms. Suitable examples include methyl, ethyl, propyl, butyl, pentyl and hexyl, and isomers thereof. For example, a $C_4$ group can be present in the form of n-butyl, iso-butyl, sec-butyl or tert-butyl. When an alkyl group is cyclic, it preferably contains from 5 to 10 carbon atoms, and may be, for example, cyclopentyl, cyclohexyl, cycloheptyl, decalin or adamantyl.

Alkoxy and alkylthio represent alkyl groups linked by an oxygen atom or a sulphur atom respectively, with the alkyl portion being as defined above.

Haloalkyl represents an alkyl group as defined above substituted by at least one halogen atom. Preferably the alkyl group comprises 1 to 6 carbon atoms, and it is preferably substituted by 1 to 6 halogen atoms, more preferably by 1 to 3 halogen atoms. Typical examples include methyl, ethyl and propyl groups substituted by 1 to 6 halogen atoms selected from chlorine, bromine and fluorine. Methyl groups substituted by 1 to 3 of these halogen atoms are preferred, for example trifluoromethyl and trichloromethyl.

Aryl represents a hydrocarbon comprising at least one aromatic ring, and may contain from 5 to 18, preferably from 6 to 14, more preferably from 6 to 10, and most preferably 6 carbon atoms. Typical aryl groups include phenyl, naphthyl, phenanthryl, anthracyl, indenyl, azulenyl, biphenylenyl, and fluorenyl groups. Particularly preferred aryl groups include phenyl, naphthyl and fluorenyl, with phenyl being most preferable.

Aryloxy and arylthio represent aryl groups linked by an oxygen atom or a sulphur atom respectively, with the aryl portion being as defined above.

Amino represents a group having the general formula —NR'R" where $R^{40}$ and R" are independently selected from hydrogen atoms and alkyl groups, When R' and R" are alkyl groups they preferably contain from 1 to 10, more preferably from 1 to 4, carbon atoms. Possible amino groups include —$NH_2$, methyl amino (i.e. —NHMe), ethyl amino, propyl amino, butyl amino, sec-butyl amino, tert-butyl amino, pentyl amino, hexyl amino, heptyl amino, octyl amino, stearyl amino, dimethyl amino (i.e. —$NMe_2$), diethyl amino, dipropyl amino, dibutyl amino, disec-butyl amino, ditert-butyl amino, dipentyl amino, dihexyl amino, diheptyl amino, dioctyl amino and distearyl amino. Mixed dialkyl amino groups (i.e. where R' and R" are different) are also possible.

Siloxy represents a group of general formula —$OSiR_3$, where each R group is independently selected from the group consisting of a hydrogen atom and an alkyl group. The alkyl group preferably has from 1 to 6, more preferably 1 to 4, carbon atoms The term ester (also known as alkoxycarbonyl) represents a group of formula —C(O)OR where R is a hydrogen atom or an alkyl group. Preferably the alkyl group has from 1 to 6, more preferably from 1 to 4, carbon atoms.

The term heterocyclic represents groups having between 3 and 20, more preferably between 3 and 10, carbon atoms and having one or more 4, 5, 6 or 7 member saturated or unsaturated rings containing 1, 2 or 3 oxygen, nitrogen or sulphur atoms. Heterocyclic groups containing saturated rings include groups based on pyrrolidine, piperidine, tetrahydro-thiophene, dithiolane, oxathiolane, oxazolidine, oxazinane, oxathiane, tetrahydro-thiopyran, tetrahydro-pyran, dioxolane, dioxane, thiazinane, dithiane, thiazolidine, imidazolidine, hexahydro-pyrimidine and tetrahydro-furan.

Heterocyclic groups containing aromatic rings (heteroaryl groups) include thienyl, benzothienyl, naphthothienyl, thianthrenyl, furyl, pyranyl, isobenzofuranyl, chromenyl, xanthenyl, phenoxathinyl, pyrrolyl, imidazolyl, pyrazolyl, pyridyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinazolinyl, cinnolinyl, pteridinyl, carbazolyl, carbonlinyl, phenanthridinyl, acridinyl, perimidinyl, phenanthrolinyl, phenazinyl, isothiazolyl, phenothiazinyl, isoxazolyl, furazanyl, quinoxalynyl, quinazolynyl, pylazinyl, acrydinyl, phenadinyl, furluryl, isochiazolyl, isoquixazolyl, phenoquisadinyl, benzthiazolyl, benzoxazylyl, benzoinidazolyl, pyranthrenyl, oparenyl and phenoxazinyl.

The term halogen represents any halogen atom selected from fluorine, chlorine, bromine and iodine, with fluorine and chlorine being preferred.

Where any of the groups defined above are described as being optionally substituted, the substituent groups may include halogen atoms, hydroxy, thiol, cyano, amino, silyl, nitro, alkyl, haloalkyl, cycloalkyloxy, alkoxy, haloalkoxy, alkoxycarbonyl, carboxyl, carbonyl, alkanoyl, alkylthio, alkylsulphinyl, sulphinyl, alkylsulphonyl, sulphonato, alkylsulphonato, aryl, arylalkyl, alkaryl, aryloxy, arylsulphinyl, arylsulphonyl, arylsulphonato, sulphonamide, carbamoyl, carbamido, alkylamido, alkenyl, alkenyloxy and alkynyl, as well as heterocyclic groups. The preferred optional substituents are halogen atoms, and nitro, hydroxy, alkyl, haloalkyl, alkoxy and carboxy groups. When the optional substituent is an alkyl, haloalkyl or alkoxy group, the alkyl portion of the substituent preferably contains from 1 to 6 carbon atoms, and is preferably linear. Particularly preferred optional substituents are chlorine atoms, and nitro, hydroxy, methyl, ethyl, tertiary butyl and methoxy groups.

The compounds and compositions disclosed in the present invention have the ability to produce a cooling sensation when in contact with the skin and/or mucosal membrane of a human or animal body. A "cooling sensation" as used throughout is thus Intended to mean any sensation of coolness which is perceived by human or animal body. Such a cooling sensation is analogous to the sensation produced by compounds such as menthol, and/or the sensation elicited when cold-sensitive receptors, such as those identified in McKemy et al, Nature, Vol. 416, 2002, 52–58, are stimulated.

A cooling sensation is desirable in many different applications. For example, the compounds and compositions of the invention have applications in a number of personal hygine, oral hygiene and food product compositions.

Personal hygiene applications include lotions, shaving cream, post shaving preparations, shampoos, conditioners, facial cleansers, soaps, bath oils and foams, antiperspirants, deodorants. Oral hygiene applications include toothpastes, mouthwashes, dental floss, chewing gum and breath fresheners. Foodstuff applications include beverages, spreads, ice-creams and confectionery. Possible other applications where a cooling sensation may be desirable include pharmaceutical products (for example chewable pharmaceutical products, or throat lozenges), tobacco products, insect repellents and cosmetics.

As stated above, a first embodiment of the invention provides the use of a compound of Formula [I] on order to produce a cooling sensation with the proviso that when $R^1$ is 2-hydroxyphenyl, $R^2$ is other than 3-nitrophenyl. In this embodiment, it has been found that preferred $R^1$ groups include optionally substituted alkyl or aryl groups. The alkyl group can be a linear group such as a $C_{1-10}$ aliphatic chain, or a cyclic group, such as a $C_{3-10}$ cyclic hydrocarbon. It is preferred that $R^1$ is an optionally substituted aryl or cyclic hydrocarbon group, such as a phenyl or cyclohexyl group.

The preferred $R^2$ groups include hydrogen atoms, or optionally substituted alkyl or aryl groups. Again, the $R^2$ group can be a linear, aliphatic chain, or a cyclic hydrocarbon, as for $R^1$. The preferred groups are optionally substituted aryl and cyclic hydrocarbon groups, with phenyl and cyclohexyl being particularly favoured. Alternatively, it may be desirable to replace these cyclic groups with other groups, such as a hydrogen atom, a straight chain alkyl group (e.g. a $C_{3-10}$ alkyl group) or a branched chain alkyl group (e.g. a tertiary butyl group).

A subset of particularly preferred compounds in the first embodiment are those according to general formula [II]:

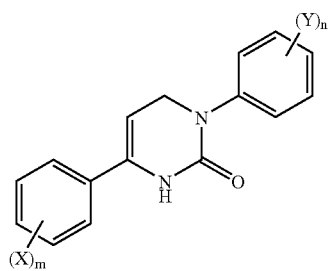

wherein the or each X and Y is independently a halogen atom or an alkyl, alkenyl, haloalkyl, alkoxy, hydroxy, thiol, carboxy, nitro, sulphonamide, sulphonato, sulphonyl, alkoxycarbonyl, carbonyl or amino group, and m and n are independently 0, 1, 2 or 3, with the proviso that when n is 1, m is 1 and Y is a hydroxy group in the ortho position, X is other than a nitro group in the meta position. Where the substituent X or Y groups contain an alkyl portion (e.g. the alkyl portion of haloalkyl), this alkyl portion preferably contains from 1 to 6 carbon atoms. In the case of an alkenyl group, this preferably contains from 2 to 6 carbon atoms.

X can be selected from any of the groups listed above, with hydrogen and halogen atoms, and nitro, hydroxy, $C_{1-6}$ alkyl, $C_{1-6}$ haloalkyl and $C_{1-6}$ alkoxy groups being preferred. The number of X substituents can vary between 0 and 3, and the point of substitution of the phenyl ring may also be varied. It is preferred that there is a single substituent on the phenyl ring, i.e. where m is 1. In this case the substituent can be present in the ortho, meta or para position, relative to the point of attachment of the phenyl ring to the rest of the molecule containing the cyclic urea group. The optimal point of attachment will depend on a number of factors, such as the nature of the substituent and its electron-donating or electron-withdrawing effect. Particularly useful compounds include those where the substituent is present in the meta position.

Similarly, Y can be selected from any of the groups listed above, with hydrogen, hydroxy, $C_{1-6}$ alkyl, $C_{1-6}$ haloalkyl and $C_{1-6}$ alkoxy groups being preferred. The number of Y substituents can vary between 0 and 3, and the point of substitution of the phenyl ring may also be varied. It is preferred that there is a single Y substituent (i.e. where n is 1), which may be present in the ortho, meta or para position, relative to the point of attachment of the phenyl ring to the rest of the molecule containing the cyclic urea group. Particularly useful compounds include those where the single Y substituent is present in the ortho position.

Thus, a particularly preferred compound in accordance with the first embodiment of the invention is one according to general formula [III]:

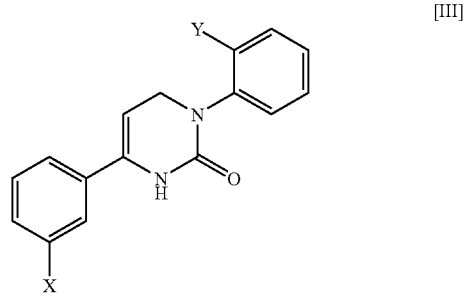

wherein X and Y are independently selected from a halogen atom or an alkyl, alkenyl, haloalkyl, alkoxy, hydroxy, thiol, carboxy, nitro or amino group, with the proviso that when Y is a hydroxy group, X is other than a nitro group. It is preferred that X is a hydrogen or halogen atom, or a nitro, hydroxy, $C_{1-6}$ alkyl or $C_{1-6}$ alkoxy group. Particularly preferred groups include halogen atoms, and methyl, ethyl, methoxy and ethoxy groups. The preferred halogen atom is chlorine.

A number of compounds have been synthesised, and show an ability to elicit a cooling sensation. Preferred compounds include 1-(2'-methoxyphenyl)-4-(3"-nitrophenyl-1,2,3,6-tetrahydropyrimidine-2-one, 1-phenyl-4-(3"-nitrophenyl)-1,2,3,6-tetrahydropyrimidine-2-one, 1-(2'-methoxyphenyl-4-(3"-chlorophenyl)-1,2,3,6-tetrahydropyrimidine-2-one, 1-phenyl-4-(3"-chlorophenyl)-1,2,3,6-tetrahydropyrimidine-2-one, 1-(2'-methylphenyl)-4-(3"-nitrophenyl)-1,2,3,6-tetrahydropyrimidine-2-one, 1-(2'-methoxyphenyl-4-(3"-methoxyphenyl)-1,2,3,6-tetrahydropyrimidine-2-one, 1-phenyl-4-(3"-methoxyphenyl)-1,2,3,6-tetrahydropyrimidine-2-one, 1-(2'-hydroxyphenyl)-4-(3"-methoxyphenyl)-1,2,3,6-tetrahydropyrimidine-2-one, 1-(2'-trifluoromethylphenyl)-4-(3"-nitrophenyl)-1,2,3,6-tetrahydropyrimidine-2-one, 1-phenyl-4-(3"-nitrophenyl)-1,2,3,6-tetrahydropyrimidine-2-one and 1-(2'-hydroxyphenyl)-4-phenyl-1,2,3,6-tetrahydropyrimidine-2-one. In particular, 1-(2'-hydroxyphenyl)-4-(3"-methoxyphenyl)-1,2,3,6-tetrahydropyrimidine-2-one, 1-(2'-trifluoromethylphenyl)-4-(3"-nitrophenyl)-1,2,3,6-tetrahydropyrimidine-2-one, 1-phenyl-4-(3"-nitrophenyl)-1,2,3,6-tetrahydropyrimidine-2-one and 1-(2'-hydroxyphenyl)-4-phenyl-1,2,3,6-tetrahydropyrimidine-2-one have shown good cooling effects.

The compounds may be used alone, or in a composition in combination with another substance or substances such as a carrier. The nature of these additional substances, and the relative proportions of components of the composition will depend on a number of factors, such as the specific use for which the composition is employed. The compositions may be used in a variety of applications, such as those discussed above. Particularly preferred uses include personal hygiene products such as deodorant, shower gel and skin cream; oral hygiene products such as toothpastes and mouthwashes; and foodstuffs, such as beverages, ice-creams, confectionery and spreads.

The second embodiment of the invention encompasses compounds of general formula [IV] recited above, or a salt thereof, wherein X is a hydrogen or halogen atom, or a hydroxy, nitro, alkyl or alkoxy group; Y is hydrogen, hydroxy, haloalkyl, nitro or alkoxy, and n is 0, 1, 2 or 3, with the proviso that when n is 1 and Y is hydroxy, X is alkyl or hydroxy. It is preferred that when n is 1 and Y is hydroxy, X is not a halogen atom. According to one aspect of this embodiment, it is preferred that when n is 1 and Y is hydroxy, X is alkyl or hydroxy. Particularly preferred in this aspect is where Y is hydroxy.

In other embodiments it is preferred that Y is haloalkyl, particularly when Y is nitro. A particularly preferred haloalkyl is halomethyl, most preferably trifluoromethyl.

The number of Y substituents may vary between 0 and 3, and the substituents can be present in any position. However, it is preferred that there is a single Y substituent, i.e. where n is 1. This substituent may be present in the ortho, meta or para position, relative to the point of attachment of the phenyl ring to the rest of the molecule. The optimal position of the substituent will depend on a number of factors, such as the nature of the substituent and its electron-donating or electron-withdrawing effect. The ortho position is preferred. Thus, particularly preferred compounds in accordance with the second embodiment are those according to the general formula [V]:

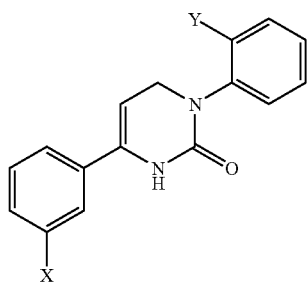

[V]

with Y being as defined above. It is preferred that Y is a hydroxy group or a methoxy group. X is preferably a hydrogen or halogen atom, or a hydroxy, $C_{1-6}$ alkyl or $C_{1-6}$ alkoxy group, providing that where Y is hydroxy, X is alkyl or hydroxy. Particularly preferred X groups include halogen atoms, and methyl, ethyl, methoxy and ethoxy groups. Chlorine atoms and methoxy groups are most preferred.

Compounds according to this embodiment which have been shown to exhibit a cooling effect include those listed above in relation to the first embodiment, particularly 1-(2'-hydroxyphenyl)-4-(3"-methoxyphenyl)-1,2,3,6-tetrahydropyrimidine-2-one, 1-(2'-trifluoromethylphenyl)-4-(3"-nitrophenyl)-1,2,3,6-tetrahydropyrimidine-2-one, 1-phenyl-4-(3"-nitrophenyl)-1,2,3,6-tetrahydropyrimidine-2-one and 1-(2'-hydroxyphenyl)-4-phenyl-1,2,3,6-tetrahydropyrimidine2-one. Most preferred are 1-(2'-hydroxyphenyl)-4-(3"-methoxyphenyl)1,2,3,6tetrahydropyrimidine-2-one and 1-(2'-trifluoromethylphenyl)-4-(3"-nitrophenyl)-1,2,3,6-tetrahydropyrimidine-2-one.

Again, the compounds of this second embodiment of the invention may be used in a variety of applications, such as those discussed above. In particular they may be used in applications similar to those described above in relation to the first embodiment of the invention, for example in personal hygiene products such as deodorant, shower gel and skin cream; oral hygiene products such as mouthwash and toothpaste; and food products. The compounds may have particularly useful applications in foodstuffs such as beverages, spreads, confectionery and ice-cream.

The third embodiment of the invention provides novel compositions comprising compounds of the invention. The compositions can be used for a number of applications where a cooling sensation is desirable. As discussed above, such applications may include the fields of personal hygiene products (including lotions, shaving cream, post shaving preparations, shampoos, conditioners, facial cleansers, soaps, bath oils and foams, antiperspirants and deodorants); oral hygiene products (including toothpastes, mouthwashes, dental floss, chewing gum and breath fresheners); food products (including beverages, spreads, ice-creams and confectionery); and other applications where a cooling sensation may be desirable (including pharmaceutical products such as chewable pharmaceutical products or throat lozenges, tobacco products, insect repellents and cosmetics).

Particularly preferred are compositions for use as toothpastes, mouthwashes and food products such as confectionery, beverages, spreads and ice-cream. The specific nature of the composition (e.g. the nature of the additional components, the relative proportions of the components and the physical nature of the composition) will depend on the particular application.

In a first aspect of the third embodiment, there is provided a composition, such as a toothpaste, mouthwash or food product composition, comprising a compound of formula [I]:

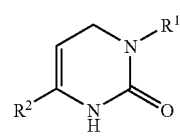

[I]

or a salt thereof to produce a cooling sensation, wherein $R^1$ and $R^2$ are independently selected from hydrogen or halogen atoms; hydroxy, cyano, nitro, mercapto, carbonyl, sulfone and carboxy groups; or optionally substituted alkyl, alkenyl, alkoxy, alkylthio, aryl, aryloxy, arylthio, amino, siloxy, ester and heterocyclic groups. In this aspect it is preferred that the compound of formula [I] is other than a compound where $R^1$ is 2-hydroxyphenyl and $R^2$ is 3-nitrophenyl.

The compound of formula [I] can be any compound resulting from a selection of $R^1$ and $R^2$ from the list given above. However, preferred compounds are those which have already been discussed in relation to the first embodiment of the invention above.

In a second aspect of this embodiment of the invention, there is provided a composition, such as a toothpaste, mouthwash or food product composition, comprising a compound of formula [IV] as discussed above in relation to the second embodiment of the invention.

In either aspect, the compound which is capable of producing a cooling sensation is preferably present in an amount of from 0.0001% to 3%, eg from 0.001% to 3% by weight, based on the total weight of the composition. An especially preferred range is from 0.0001% to 0.3% by weight. The compound may present in an amount of from 0.0003% to 0.1% or from 0.003% to 0.1%.

The compounds disclosed above in all embodiments of the invention can be made according to a general process shown in Scheme 1:

Scheme 1

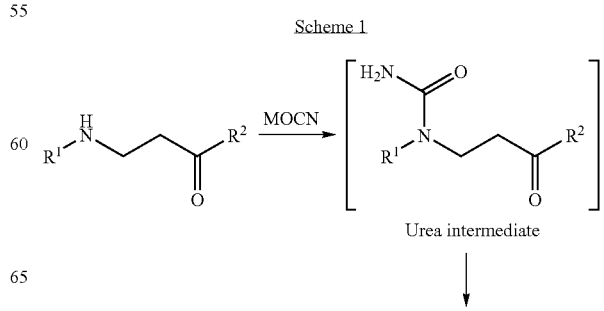

Urea intermediate

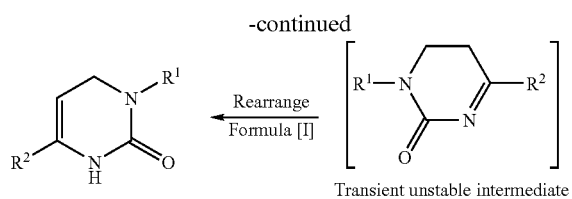

Transient unstable intermediate

The β-amino-ketone compound required in Scheme 1 can be made by any suitable process, for example according to the synthetic route described in Examples 1 and 2 below, or via the synthetic routes disclosed in the examples of U.S. Pat. No. 3,821,221.

Preferred embodiments of the invention will now be described by way of example only. Further modification within the scope of the present invention will be apparent to the person skilled in the art.

EXAMPLES

Example 1

Preparation of dimethylamino-m-chloropropiophenone Hydrochloride

To a solution of tetramethyldiaminomethane (15.0 ml, 0.11 mol) in acetonitrile (350 ml) under nitrogen was added dropwise a solution of acetyl chloride (7.8 ml, 0.11 mol) in acetonitrile (7.83 ml) at room temperature. After the addition, stirring was continued for one hour and then 3'-chloroacetophenone (20.0 g, 0.13 mol) was added over 5 minutes. The reaction mixture was refluxed for 2 hours, cooled to room temperature and the white precipitate that formed was filtered off, washed with cold acetonitrile and dried under vacuum (22.9 g, 84%).

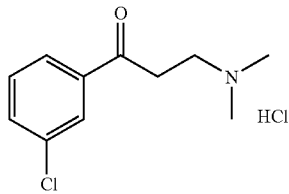

$^1$H NMR (d$^6$-DMSO, 500 MHz)$\delta_H$ 2.80 (6H, s, 2×CH$_3$), 3.39 (2H, t, CH$_2$, $^3J_{HH}$=7.25 Hz), 3.64 (2H, t, CH$_2$, $^3J_{HH}$=6.94 Hz), 7.61 (1H, dd, H$_c$, $^3J_{HcHb}$=7.89 Hz), $^3J_{HcHb}$=7.88 Hz, 7.77 (1H, ddd, H$_b$, $^3J_{HbHc}$=7.88 Hz, $^4J_{HbHd}$=2.20 Hz, $^4J_{HbHa}$=0.94 Hz), 7.97 (1H, ddd, H$_d$, $^3J_{HdHc}$=7.88 Hz, $^4J_{HdHb}$=0.95 H$_z$, $^4J_{HdHa}$=1.58 Hz), 8.04 (1H, dd, H$_a$, $^4J_{HdHa}$=1.89 Hz, $^4J_{HaHd}$=1.89 Hz).

Example 2

Preparation of β-(o-hydroxyanilino)-m-chloropropiophenone Hydrochloride

Dimethylamino-m-chloropropiophenone hydrochloride (74.9 g, 0.30 mol) was dissolved in 50% aqueous ethanol (700 ml) at reflux. 2-Aminophenol (32.9 g, 0.30 mol) was then added and the resulting red solution was refluxed for a further 2 hours. The reaction mixture was allowed to cool to room temperature and then extracted twice with ethyl acetate (2×100 ml). Note that brine was also added at this point to allow the two layers to separate effectively). The organic extracts were combined and an excess of concentrated hydrochloric acid (47 ml) was added. The solution was concentrated in vacuo and then allowed to cool. The precipitate that formed was filtered of, washed with diethyl ether and dried in vacuo to yield a cream powder (38.1 g, 40%).

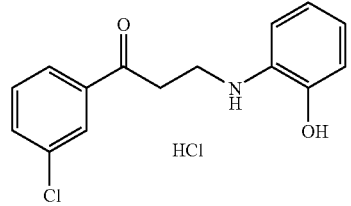

$^1$H NMR (d$^6$-DMSO, 500 MH$_z$) $\delta_H$ 7.92 (1H, m, H$_d$), 7.90 (1H, dd, H$_a$, $^4J_{HaHb}$=1.58 Hz, $^4J_{HaHd}$=1.26 Hz), 7.75 (1H, ddd, H$_b$, $^3J_{HbHc}$=7.89 Hz, $^4J_{HbHd}$=0.95 Hz, $^4J_{HbHa}$=1.90 Hz), 7.60 (1H, dd, H$_c$, $^3J_{HcHb}$=7.88 Hz, $^3J_{HcHd}$=8.20 Hz), 7.43 (1H, d, H$_j$, $^3J_{HjHi}$=7.89 Hz), 7.19 (1H, t, H$_h$, $^3J_{HhHi}$=7.57 Hz, $^3J_{HhHg}$=7.25 Hz), 7.06 (1H, d, H$_g$, $^3J_{HgHh}$=8.20 Hz), 6.88 (1H, ddd, H$_i$, $^3J_{HiHj}$=7.56 Hz, $^3J_{HiHj}$=7.88 Hz, $^4J_{HiHg}$=1.26 Hz), 3.57 (4H, m, 2×CH$_2$).

Example 3

Preparation of 1-(2'-hydroxyphenyl)-4-(3"-chlorophenyl)-1,2,3,6-tetrahydro-pyrimidine-2-one β-(o-Hydroxyanilino)-m-chloropropiophenone hydrochloride (4.0 g, 0.013 mol) was taken up in acetic acid (50 ml) and the mixture was warmed to 60° C. Potassium cyanate (2.6 g, 0.032 mol) was added and the resulting reaction mixture was kept at 60° C. for a further 30 minutes and then allowed to cool to room temperature. Water (100 ml) was then added and the suspension was extracted with ethyl acetate (3×30 ml) and the combined organic extracts were washed successively with 10% sodium hydroxide solution (100 ml), 10% hydrochloric acid (100 ml) and brine (100 ml). The organic extract was the dried (Na$_2$SO$_4$), concentrated in vacuo and allowed to cool overnight. The precipitate that formed was filtered off and washed with diethyl ether to yield a cream powder (1.6 g, 41%).

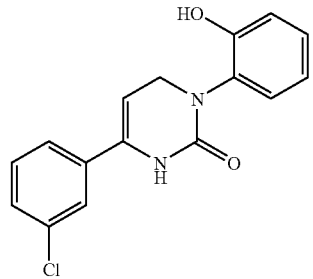

$^1$H NMR (d$^6$-DMSO, 500 MHz) $\delta_H$ 9.55 (1H, s, NH), 8.70 (1H, s, OH), 7.63 (1H, s, H$_a$), 7.54 (1H, m, H$_c$), 7.42 (2H, m, H$_b$, H$_d$), 7.18 (1H, d, H$_j$, $^3J_{HjHi}$=7.57 Hz), 7.12 (1H, ddd, H$_h$, $^3J_{HhHi}$, =7.57 Hz, $^3J_{HhHg}$=7.88 Hz, $^4J_{HhHj}$=1.57 Hz), 6.91 (1H, d, H$_g$, $^3J_{HgHh}$=8.20 Hz), 6.81 (1H, dd, H$_i$, $^3J_{HiHj}$=7.57 Hz, $^3J_{HiHh}$=7.57 Hz), 5.30 (1H, m, H$_e$), 4.25 (2H, m, H$_f$).

Example 4

The efficacy of different compounds according to the invention was tested in vitro, by exposing cultured neurons to the compounds and monitoring the cellular Ca$^{2+}$ levels.

The compounds tested include a number according to the following general formula:

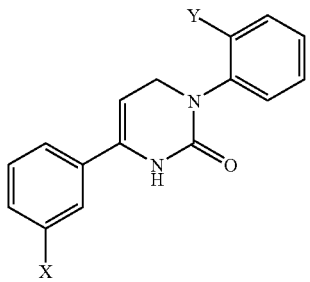

The following specific compounds were tested, along with menthol as a comparative example:

| Compound Number | X | Y |
|---|---|---|
| 1 | NO$_2$ | OH |
| 2 | CH$_3$ | OH |
| 3 | Cl | OH |

The compounds were dissolved in DMSO by ultrasonication to a 0.1 M solution. 5 μl of this stock was added to 5 mg of cyclodextrin and 5 ml of 140 Na-tyrode, to achieve a 100 μM final test concentration.

Neurons from trigeminal ganglia of Wistar rats were prepared as described in U.S. Pat. No. 5,811,256. After 24 hours of cultivation, the responsiveness of the neurons to different compounds was measured according to the general procedure described by McKemy et al (Nature, Vol. 416, 2002, 52–58). The test protocol described by McKemy was modified slightly, by using the fluorescent Ca$^{2+}$ indicator Fura-2. Detection of the cellular fluorescence signals was performed by videomicroscopical analysis. The neurons were given a cold stimulus by a thermocoupling device and were subsequently tested for responsiveness to the test compounds by superfusion with solutions containing the test compounds while continuously monitoring the cellular Ca$^{2+}$ levels.

The results were recorded for compounds 1 to 3 and menthol, and are expressed below, as a percentage compared to the activity for compound 1 (icilin).

| Compound | Activity (% relative to Compound 1) |
|---|---|
| 1 | 100 |
| 2 | 40 |
| 3 | 35 |
| Menthol (comparative example) | 42 |

It can be seen that compounds according to the invention are effective in producing sensations of coolness when they are brought into contact with cultured neurons. It can be expected that the in vitro efficacy displayed in the above tests will also be achieved when the compounds are brought into contact with the human body (for example, the skin and/or mucosal membranes), thus providing a sensation of coolness.

The invention claim is:

1. A compound of formula [IV]:

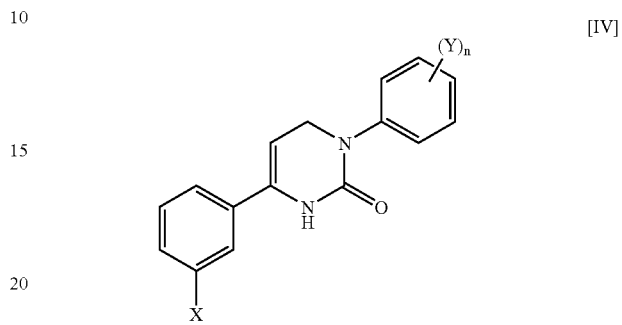

or a salt thereof, wherein X is a hydrogen or halogen atom, or a hydroxy, nitro, alkyl or alkoxy group; Y is hydrogen, hydroxy, haloalkyl, nitro or alkoxy; and n is 0, 1, 2 or 3, with the proviso that when n is 1 and Y is hydroxy, X is not nitro.

2. The compound of claim 1, with the proviso that when n is 1 and Y is hydroxy, X is not a halogen atom.

3. The compound of claim 1, wherein Y is hydroxy or alkoxy, with the proviso that when n is 1 and Y is hydroxy, X is alkyl or hydroxy.

4. The compound of claim 1, wherein n is 1.

5. The compound of claim 1, wherein n is 1 and Y is hydroxy.

6. The compound of claim 1, wherein Y is haloalkyl.

7. The compound of claim 6, wherein Y is trifluoromethyl.

8. The compound of claim 1, having the formula [V]:

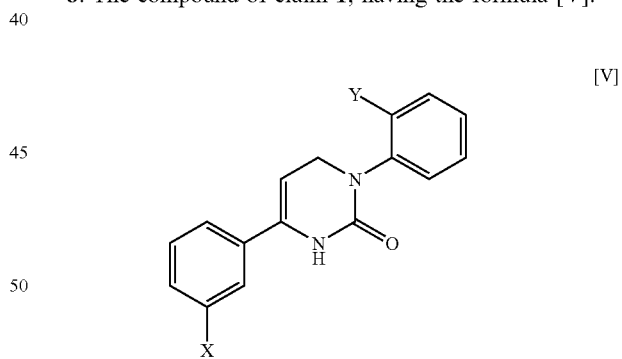

wherein Y is C$_{1-6}$ alkoxy.

9. The compound of claim 1, wherein X is a chlorine atom or a methoxy group.

* * * * *

UNITED STATES PATENT AND TRADEMARK OFFICE
CERTIFICATE OF CORRECTION

PATENT NO. : 7,045,624 B2 Page 1 of 1
APPLICATION NO. : 10/664367
DATED : May 16, 2006
INVENTOR(S) : Alison Jane Foster, Cornelius Paul Erik Van Der Logt and Erwin Werner Tareilus It is certified that error appears in the above-identified patent and that said Letters Patent is hereby corrected as shown below:

On the Title page Item (54) col. 1
The Title should be replaced by

--NOVEL COMPOUNDS AND THEIR USES--

Signed and Sealed this

Twenty-second Day of August, 2006

JON W. DUDAS
*Director of the United States Patent and Trademark Office*